United States Patent
Ohnishi et al.

(10) Patent No.: US 8,494,605 B2
(45) Date of Patent: Jul. 23, 2013

(54) NON-INVASIVE BLOOD COMPONENT MEASURING DEVICE AND A COMPUTER PROGRAM PRODUCT

(75) Inventors: Yasuhito Ohnishi, Kakogawa (JP); Toshiyuki Ozawa, Miki (JP)

(73) Assignee: Sysmex Corporation, Kobe (JP)

( * ) Notice: Subject to any disclaimer, the term of this patent is extended or adjusted under 35 U.S.C. 154(b) by 1167 days.

(21) Appl. No.: 12/378,101

(22) Filed: Feb. 11, 2009

(65) Prior Publication Data

US 2009/0203976 A1 Aug. 13, 2009

(30) Foreign Application Priority Data

Feb. 12, 2008 (JP) .................................. 2008-030172

(51) Int. Cl.
*A61B 5/00* (2006.01)
*G06K 9/00* (2006.01)

(52) U.S. Cl.
USPC ............................ 600/321; 382/128; 600/328

(58) Field of Classification Search
USPC .................... 600/322–341; 382/128
See application file for complete search history.

(56) References Cited

U.S. PATENT DOCUMENTS

| 7,280,860 | B2 | 10/2007 | Ikeda et al. | |
| 7,859,573 | B2 * | 12/2010 | Subbotin et al. | 348/221.1 |
| 8,185,177 | B2 * | 5/2012 | Numada et al. | 600/322 |
| 2007/0015980 | A1 * | 1/2007 | Numada et al. | 600/322 |
| 2008/0081968 | A1 * | 4/2008 | Numada et al. | 600/322 |

FOREIGN PATENT DOCUMENTS

JP 2007-044491 2/2007

* cited by examiner

*Primary Examiner* — Max Hindenburg
*Assistant Examiner* — John Pani
(74) *Attorney, Agent, or Firm* — Brinks Hofer Gilson & Lione (57) ABSTRACT

A noninvasive blood component measuring device configured so as to resolve the variance of measuring results depend on the fixing position to the living body. Concretely, a non-invasive blood component measuring device comprising a light source section for illuminating a living body which includes a blood vessel, an imaging section for imaging the living body illuminated by the light source, and a controller is disclosed. The controller includes a memory under control of a processor. The memory stores instructions enabling the processor to carry out following operations: calculating a blood component concentration based on a blood vessel in a living body image obtained by the imaging section imaging a living body; determining the position of the blood vessel in the living body image; preparing at least a first luminance distribution which is distributed along the blood vessel based on the position of the blood vessel; obtaining an index which reflects the amount of blood contained in the peripheral tissue of the blood vessel based on the first luminance distribution; and correcting the blood component concentration based on the index. Non-invasive blood component measuring method and a computer program product capable of achieving above mentioned function are also disclosed.

10 Claims, 12 Drawing Sheets

NON-INVASIVE BLOOD COMPONENT MEASURING DEVICE AND A COMPUTER PROGRAM PRODUCT

RELATED APPLICATIONS

This application claims priority under 35 U.S.C. §119 to Japanese Patent Application No. JP2008-030172 filed on Feb. 12, 2008, the entire content of which is hereby incorporated by reference.

FIELD OF THE INVENTION

The present invention relates to a non-invasive blood component measuring device, a non-invasive blood component measuring method and a computer program product.

BACKGROUND

Non-invasive living body measuring devices, such as, for example, the device disclosed in JP2007-44491, are known as devices which measure the blood component concentrations by imaging a living body using an imaging means, and analyzing the blood vessels within the imaging region of the living body. The device disclosed in JP2007-44491 is configured by a light source section for illuminating a blood vessel (vein) in the wrist of a user, an imaging section for imaging the wrist which is illuminated by the light source section, and a control section for analyzing the blood components flowing through the blood vessel based on the captured image.

The control section analyzes the living body image captured by the imaging section, and determines the concentrations of the components in the blood based on the luminance of the blood vessel part in the living body image which contains a blood vessel. There are instances, however, when luminance of the blood vessel part within a captured image will fluctuate depending on the amount of fluid in the peripheral tissue because the light emitted from the light source is absorbed by the fluid of the peripheral tissue as well as by the blood flowing through the blood vessel. To eliminate this problem the device disclosed in Japanese Laid-Open Patent Publication No. 2007-44491 obtains optical information related to the fluid of the peripheral tissue, and calculates the blood component concentrations based on the obtained optical information.

However, the device disclosed in Japanese Laid-Open Patent Publication No. 2007-44491 detects the optical information from a fixedly determined position relative to the position at which the device is anchored.

SUMMARY OF THE INVENTION

The scope of the invention is defined solely by the appended claims, and is not affected to any degree by the statements within this summary.

A first aspect of the invention is a non-invasive blood component measuring device comprising: a light source section for illuminating a living body which includes a blood vessel; an imaging section for imaging the living body illuminated by the light source; a controller, including a memory under control of a processor, the memory storing instructions enabling the processor to carry out operations, comprising: a step of calculating a blood component concentration based on a blood vessel in a living body image obtained by the imaging section imaging a living body; a step of determining the position of the blood vessel in the living body image; a step of preparing at least a first luminance distribution which is distributed along the blood vessel based on the position of the blood vessel; a step of obtaining an index which reflects the amount of blood contained in the peripheral tissue of the blood vessel based on the first luminance distribution; and a step of correcting the blood component concentration based on the index.

A second aspect of the invention is a non-invasive blood component measuring method comprising: a step of illuminating a living body containing a blood vessel; a step of imaging the living body illuminated by the light source; a step of calculating a blood component concentration based on a blood vessel in a living body image obtained by imaging a living body; a step of determining the position of the blood vessel in the living body image; a step of preparing at least a first luminance distribution which is distributed along the blood vessel based on the position of the blood vessel; a step of obtaining an index which reflects the amount of blood contained in the peripheral tissue of the blood vessel based on the first luminance distribution; and a step of correcting the blood component concentration based on the index.

A third aspect of the invention is a computer program product comprising: a computer readable medium; and instructions, on the computer readable medium, adapted to enable a non-invasive blood component measuring device, comprising a light source section for illuminating a living body containing a blood vessel and an imaging section for imaging the living body which is illuminated by the light source section, to perform operations, comprising: a step of calculating a blood component concentration based on a blood vessel in a living body image obtained by the imaging section imaging a living body; a step of determining the position of the blood vessel in the living body image; a step of preparing at least a first luminance distribution which is distributed along the blood vessel based on the position of the blood vessel; a step of obtaining an index which reflects the amount of blood contained in the peripheral tissue of the blood vessel based on the first luminance distribution; and a step of correcting the blood component concentration based on the index.

DETAILED DESCRIPTION OF THE PREFERRED EMBODIMENTS

Hereinafter, embodiments of a sample analyzer of the invention will be described in detail with reference to the accompanying drawings.

An embodiment of the non-invasive blood component measuring device of the present invention is described in detail below with reference to the accompanying drawings.

Figure 1:
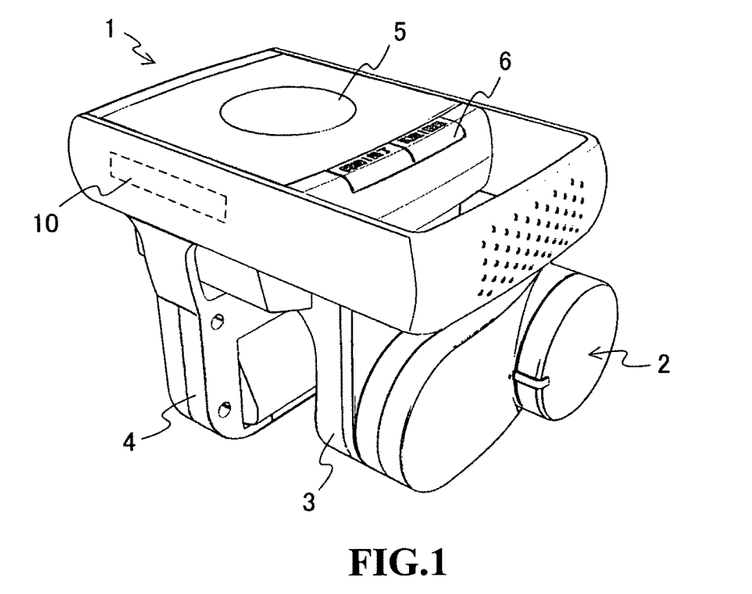
FIG. 1 is a perspective view showing the exterior of a non-invasive blood component measuring device.
Figure 2:
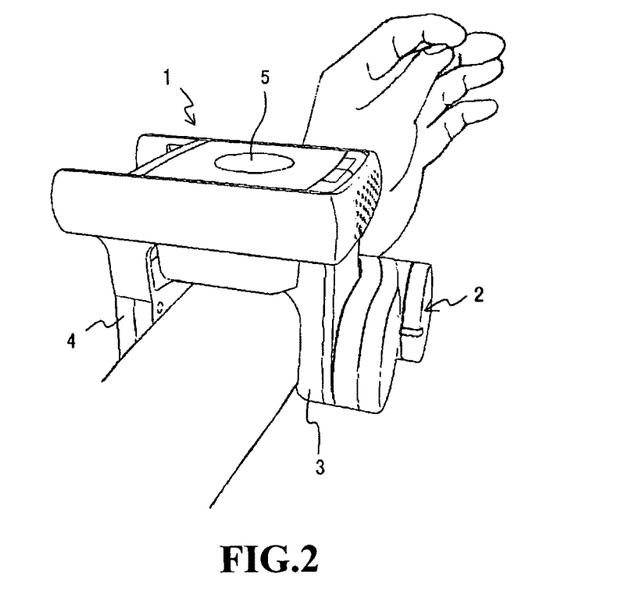
FIG. 2 is a perspective view showing an example of the usage conditions of the non-invasive blood component measuring device.

FIG. 1 is a perspective view showing the exterior of the device of the present embodiment. FIG. 2 illustrates the usage conditions of the device 1 of the present embodiment. As shown in FIG. 2, the device 1 is a blood component measuring device for imaging the blood vessels present in the wrist of an arm on which the device is installed on the arm of a user, and measuring the hemoglobin concentration based on the captured image.

The device 1 is provided with a detecting section 2, first gripping part 3, second gripping part 4, display section 5, operation section 6, and control section 10. The detecting section 2 is a mechanism for illuminating and imaging the surface of a living body, and is configured by a light source section 7 for illuminating a part of a living body on the inner side, and an imaging section 8 for imaging the part of the living body which is illuminated by the light source section 7 (refer to FIG. 3). The first gripping part 3 and the second gripping part 4 anchor the device 1 on the arm when the arm of a user is interposed therebetween as shown in FIG. 2. The display section 5 is configured by a liquid crystal panel for displaying the results of the hemoglobin concentration measurement, operation information and the like. The operation section 6 is configured by operation buttons which are operated by the user. The control section 10 controls the operation of the various parts of the device 1.

Figure 3:
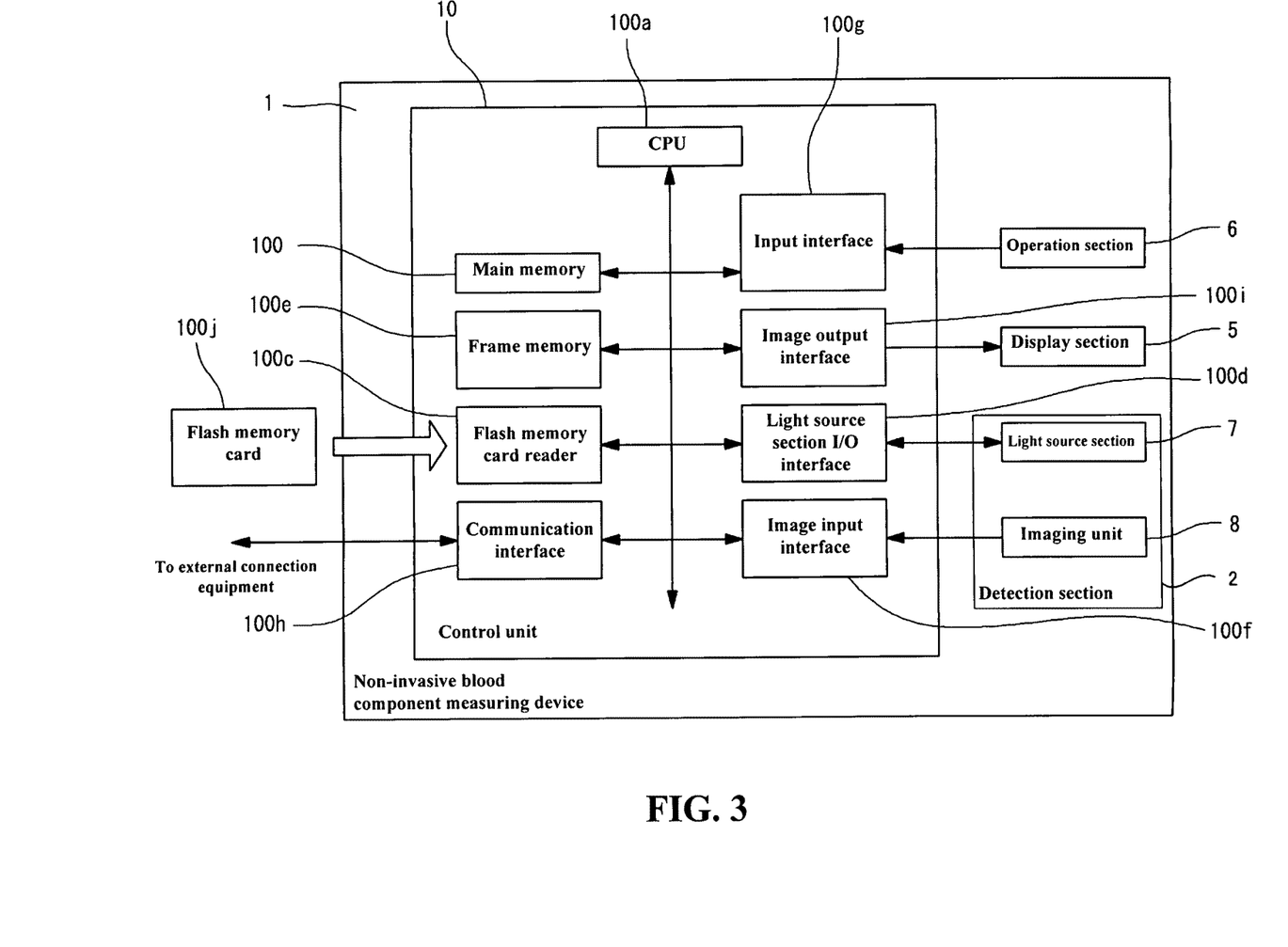
FIG. 3 is a block diagram showing the structure of the non-invasive blood component measuring device.

FIG. 3 is a block diagram showing the structure of the device 1. The control section 10 is configured by a CPU 100a, main memory 100b, flash memory card reader 100c, light source section input/output interface 100d, frame memory 100e, image input interface 100f, input interface 100g, communication interface 100h, and image output interface 100i. The CPU 100a, main memory 100b, flash memory card reader 100c, light source section input/output interface 100d, frame memory 100e, image input interface 100f, input interface 100g, communication interface 100h, and image output interface 100i are connected through a data transmission line so as to be capable of mutual data transmission. According to this construction, the CPU 100a reads and writes data from/to the main memory 100b, flash memory card reader 100c, and frame memory 100d, and sends and receives data to/from the light source section input/output interface 100d, image input interface 100f, input interface 100g, image output interface 100i, and communication interface 100h.

The CPU 100a is capable of executing computer programs which are loaded in the main memory 100b. The present device functions as a device when the CPU 100a executes a computer program which is described later.

The main memory 100b is configured by SRAM, DRAM or the like. The main memory 100b is used for reading the computer program stored on a flash memory card 100j. The main memory 100b is also used as the work area of the CPU 100a when such computer programs are executing.

The flash memory card reader 100c is used for reading data stored on the flash memory card 100j. The flash memory card 100j has a flash memory (not shown in the drawing), and is capable of retaining data without being externally supplied with power. Computer programs executed by the CPU 100a and the data used therewith and the like are stored on the flash memory card 100j.

An operating system such as, for example, the TRON specification-compliant operating system is installed on the flash memory card 100j. Note that the operating system is not limited to the above example inasmuch as an operating system which provides a graphical user interface environment such as, for example, Microsoft Windows (registered trademark of Microsoft Corporation, USA) may also be used. In the following description, the computer programs of the present embodiment operate on such an operating system.

The light source section input/output interface 100d is configured by an analog interface such as a D/A converter, A/D converter or the like. The light source section input/output interface 100d is electrically connected to the four light-emitting diodes R1, R2, L1, and L2, respectively, which are provided in the light source section 7 via electrical signal lines, and is capable of controlling the operation of the various light-emitting diodes. The light source section input/output interface 100d also controls the current supplied to the light-emitting diodes R1, R2, L1, and L2 based on a computer program which will be described later.

The frame memory 100e is configured by an SRAM, DRAM or the like. The frame memory 100e is used for storing data when the image input interface 100f which will be described later executes image processing.

The image input interface 100f is provided with a video digitizer circuit (not shown in the drawing) which includes an A/D converter. The image input interface 100f is electrically connected to the imaging section 8 via an electrical signal line so as to receive image signals sent from the imaging section 8. The image signals received from the imaging section 8 are subjected to A/D conversion by the image input interface 100f. The digitally converted image data are then stored in the frame memory 100e.

The input interface 100g is configured by an analog interface which is an A/D converter. The operation section 6 is electrically connected to the input interface 100g. According to this configuration, the user can turn the power source of the device ON/OFF and select the operation item of the device using the operation section 6, so as to allow the selected operation to be realized by the device.

The communication interface 100h is configured by a serial interface such as, for example, a USB, IEEE 1394, RS232, or the like, or a parallel interface such as, SCSI or the like. The control section 10 is capable of sending and receiving data between externally connected devices such as mobile computers and portable telephones and the like using a predetermined communication protocol via the communication interface 100*h*. Accordingly, the control section 10 sends the measurement result data to externally connected devices through the communication interface 100*h*.

The image output interface 100*i* is electrically connected to the display section 5, and outputs image signals based on the image data received from the CPU 100*a*.

Figure 4:
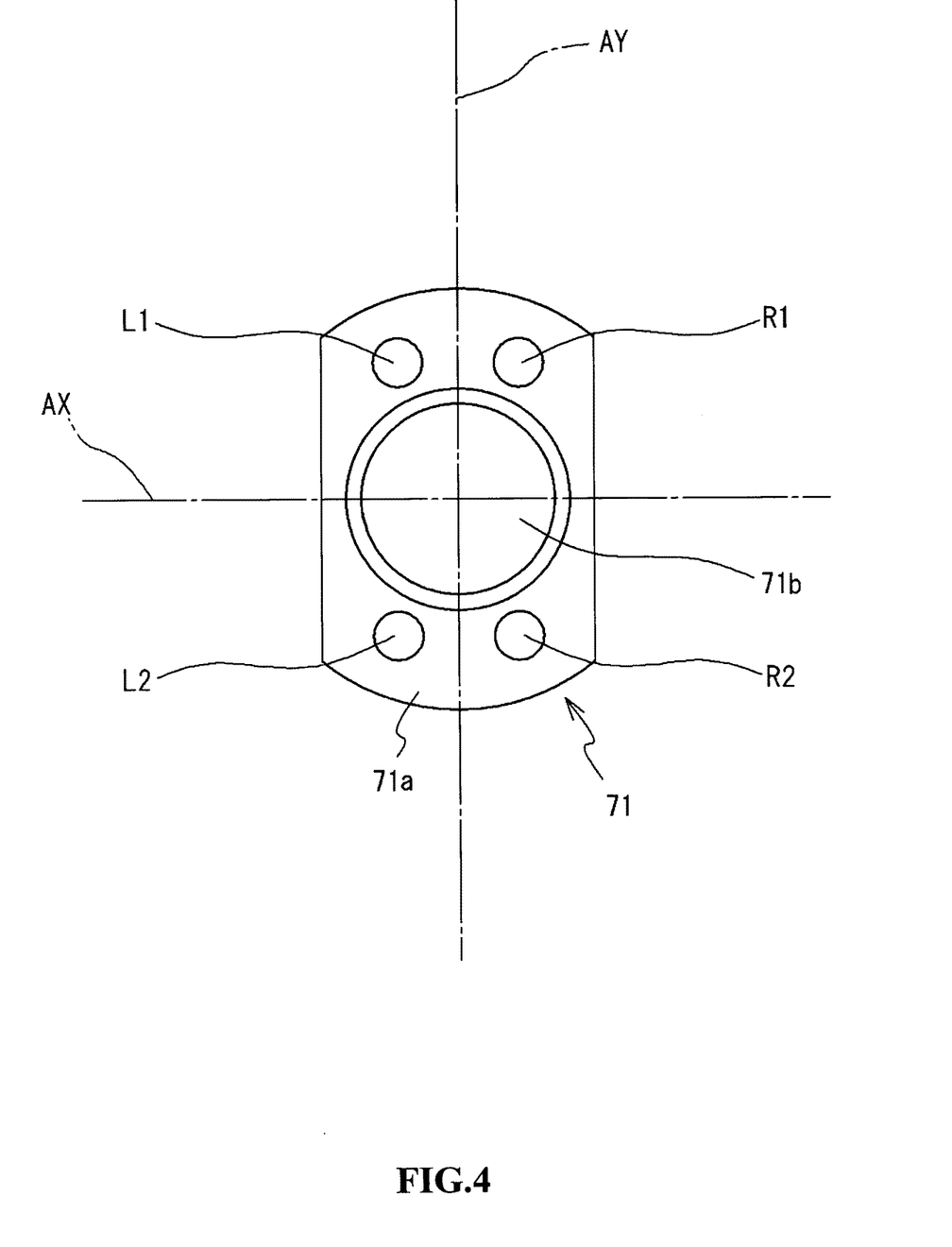
FIG. 4 is a top view showing the structure of the light source section.

FIG. 4 is a top view showing the structure of the light source section 7. The light source section 7 is configured by a retaining plate 71*a* which is approximately rectangular in shape and the short sides are rounded, and the four light-emitting diodes R1, R2, L1, and L2 are retained on the retaining plate 71*a*. A circular aperture 71*b* is formed in the center of the retaining plate 71*a* to allow entering light to pass through to the imaging section 8, and the light-emitting diodes are disposed in the margin of this aperture 71*b*.

Figure 5:
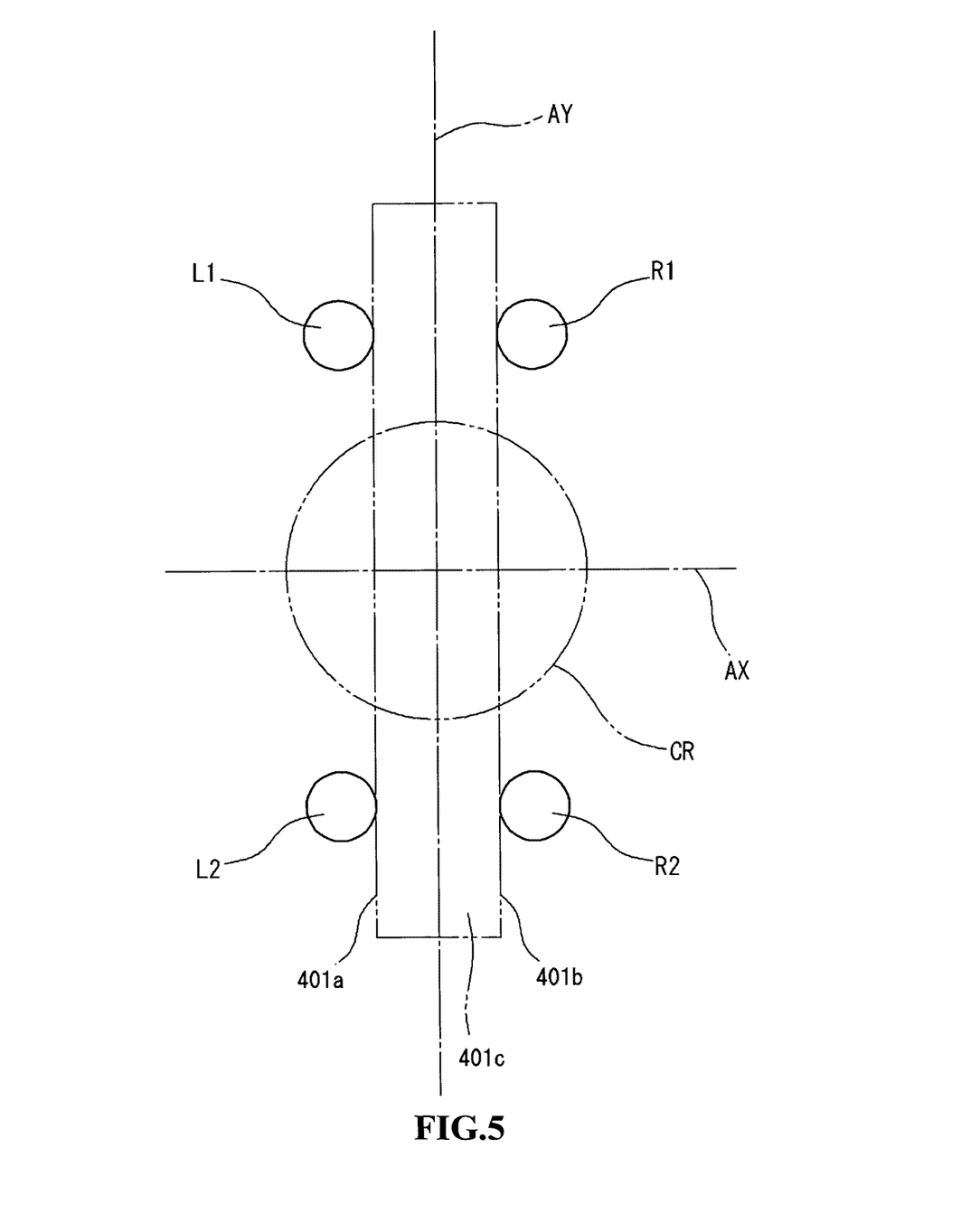
FIG. 5 illustrates the positional relationships among the four light-emitting diodes provided on a retaining plate.

FIG. 5 illustrates the positional relationships among the four light-emitting diodes provided on the retaining plate 71*a*. The light-emitting diodes R1, R2, L1, and L2 are disposed symmetrically to a first axis AY and second axis AX which mutually intersect at the center of the aperture 71*b*. When the device 1 is mounted on a wrist, the imaging region CR of the wrist surface is imaged by the imaging section 8, and this region is displayed on the display section 5. A region 401*c*, which is located between an index line 401*a* on the light-emitting diodes L1 and L2 (second light source section) side and an index line 401*b* on the light-emitting diodes R1 and R2 (first light source section) side, is the region that is suitable for imaging by the imaging section 8, that is, the region in which the blood vessel is positioned when imaging. When measuring blood components, the mounting position of the device 1 is adjusted to position an optional blood vessel of the wrist within the region 401*c*. The blood vessel is illuminated by near-infrared light (center wavelength=805 nm) via the light-emitting diodes R1, R2, L1, and L2, and the imaging section 8 images the illuminated blood vessel. Since the light-emitting diodes R1, R2, L1, and L2 are disposed above and below the paper surface of the imaging region 401*c*, the image captured by the imaging section 8 is light on the top and bottom and dark near the center, (refer to FIG. 7.

The imaging section 8 is disposed so that the retaining plate 71*a* is interposed between the living body and the imaging section 8 when the device 1 is mounted on the living body. The imaging section 8 captures a living body image through the aperture 71*b* provided in the center of the retaining plate 71*a*, and transmits the image signals to the control section 10.

Measurement Operation of the Device 1

Figure 6:
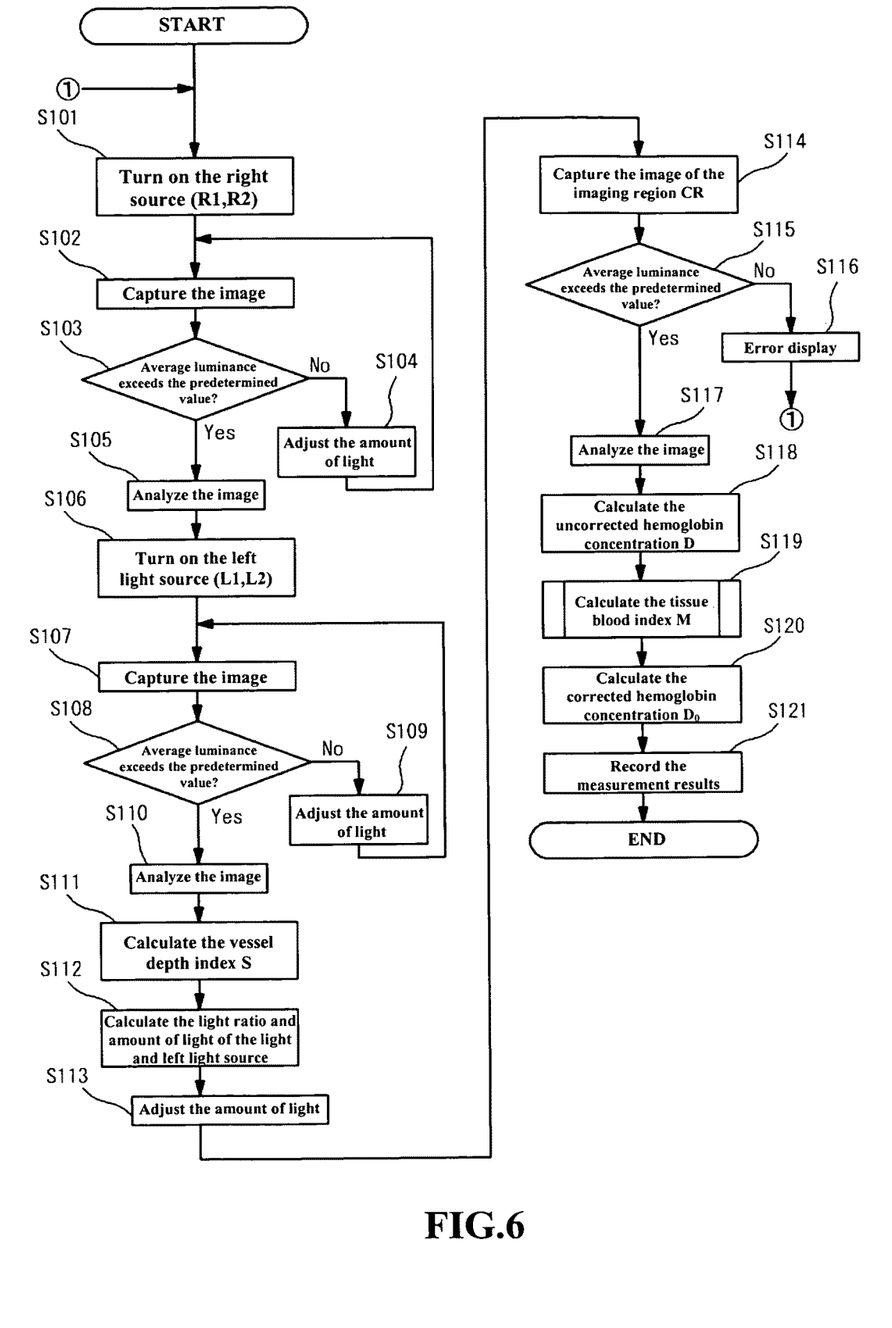
FIG. 6 is a flow chart showing the measurement operation performed by the non-invasive blood component measuring device.

The measurement operation of the device 1 is described below with reference to FIG. 6. FIG. 6 is a flow chart showing the details of the hemoglobin concentration measurement process performed by the CPU 100*a*.

The device 1 is first mounted on the arm of a user (refer to FIG. 2). When the power is then turned on to the device 1 when the user operates the operation section 6, the CPU 100*a* executes a process to display the positional adjustment on the display section 5 so as to position a blood vessel of the wrist within the region 401*c* (refer to FIG. 5) which is suitable for imaging by the imaging section 8. When the operation section 6 is operated to issue an instruction to execute a hemoglobin concentration measurement after the user has adjusted the position according to the display on the display section 5, the CPU 100*a* executes the hemoglobin concentration measurement process based on a predetermined program.

Figure 7:
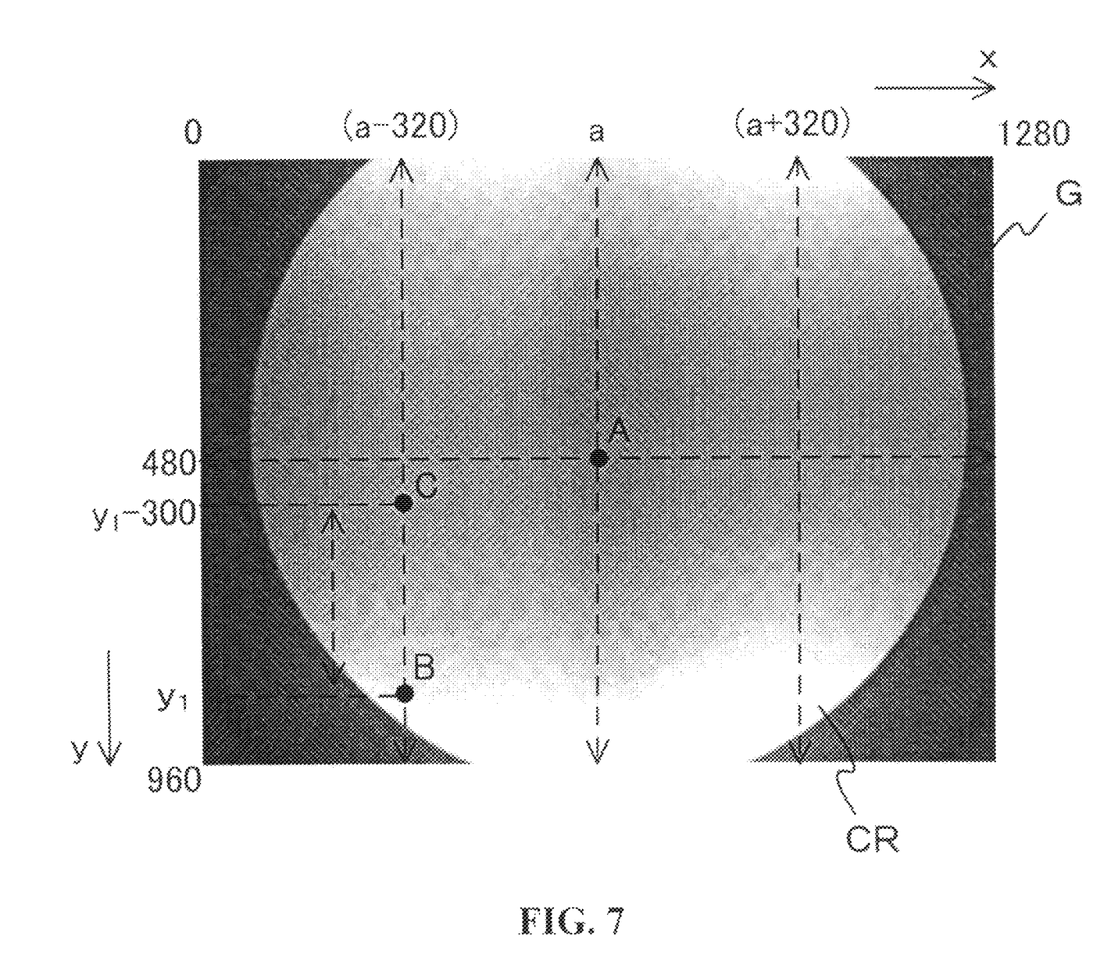
FIG. 7 shows an example of a captured image which contains a blood vessel.

FIG. 7 illustrate an example of an image obtained when the imaging section 8 images a living body, and the image is divided into two-dimensional x and y coordinates in the range wherein $0 \leq x \leq 1280$ and $0 \leq y \leq 960$. The hemoglobin concentration measurement process is described below using FIGS. 6 and 7.

The CPU 100*a* first controls the light source input/output interface 100*d*, to illuminate the living body which includes a blood vessel with a predetermined amount of light by the light-emitting diodes R1 and R2 of one light source section (first light source section) among the light sources disposed bilaterally to interpose the blood vessel therebetween (step S101), and the imaging is performed by the imaging section 8 (step S102). The CPU 100*a* determines whether or not the average luminance of the captured image G exceeds a predetermined value (step S103), and when the luminance does not exceed the predetermined value, there is an adjustment of the amount of current flowing to the light-emitting diodes R1 and R2 through the light source section input/output interface 100*d* to adjust the amount of light (step S104), whereupon the process returns to step S102.

Figure 8:
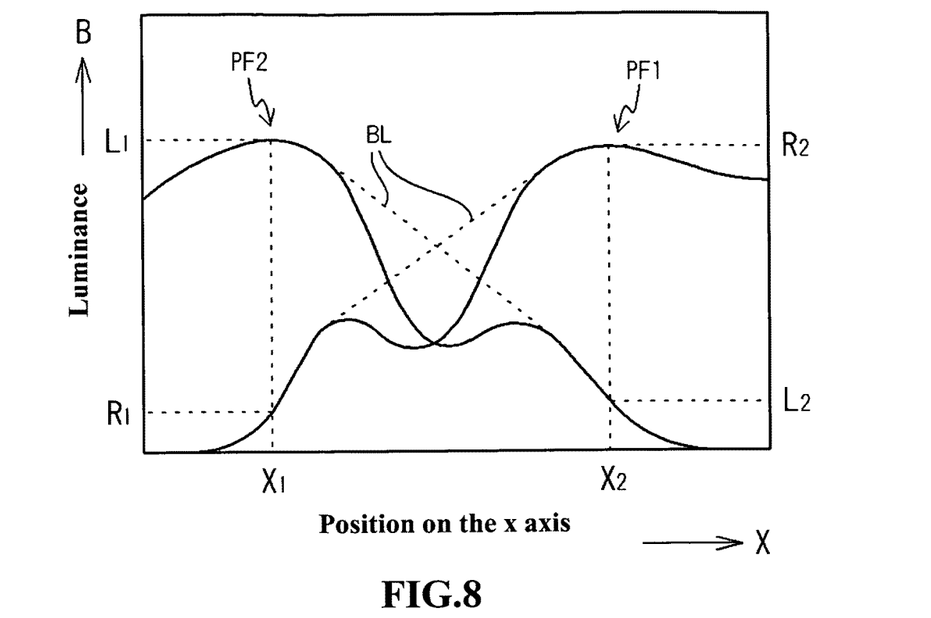
FIG. 8 shows the luminance distribution in a direction which transects the blood vessel at the y coordinate value (480) of the captured image G.
Figure 9:
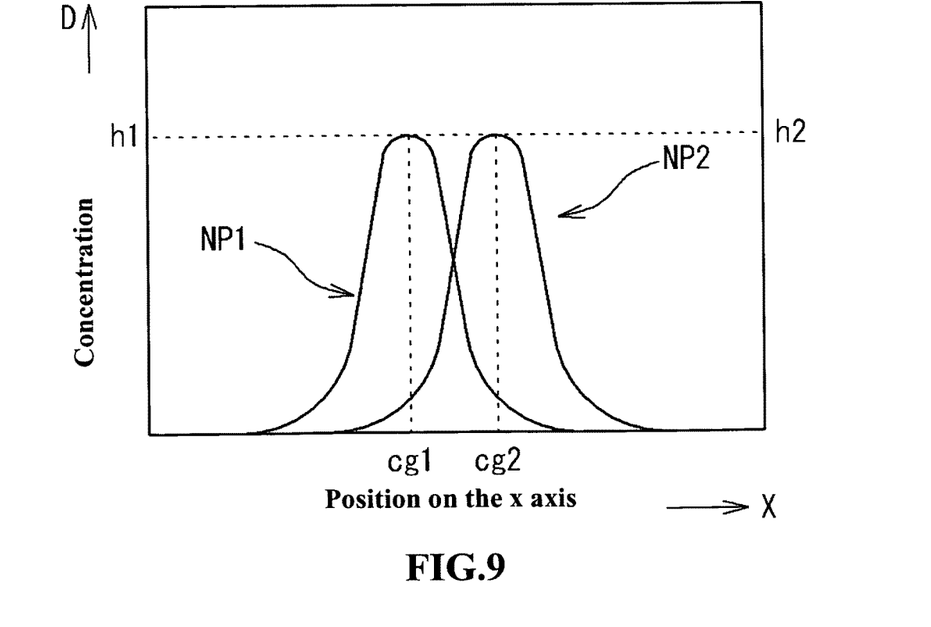
FIG. 9 shows the distribution of hemoglobin concentration in a direction which transects the blood vessel at the y coordinate value (480) of the captured image G.

FIG. 8 shows the distribution of the luminance in the horizontal direction at the y coordinate (480) of the captured image G. FIG. 9 shows the distribution of the hemoglobin concentration in the horizontal direction at the y coordinate (480) of the captured image G. When the CPU 100*a* determines that the average luminance of the captured image G exceeds the predetermined value (step S103: YES), the y coordinate value of the calculation object of the image obtained in step S102 is set at (480) which becomes the center in the y axis direction of the captured image G, then the luminance values are determined from end to end at the y coordinate value (480), and a luminance profile PF1 is prepared which has a distribution in a direction which transects the blood vessel as shown in FIG. 8. The CPU 100*a* then reduces the noise component of the obtained luminance profile PF1 using a high-speed Fourier transform method, and thereafter standardizes the luminance profile PF1 at baseline BL to prepare a concentration profile NP1 which is independent of the amount of entering light as shown in FIG. 9 (step S105).

The CPU 100*a* then controls the light source section input/output interface 100*d* to illuminate the living body which includes the blood vessel with a suitable amount of light by the light-emitting diodes L1 and L2 of the other light source section (second light source section) among the light sources disposed bilaterally to interpose the blood vessel therebetween (step S106), and the imaging is performed by the imaging section 8 (step S107). The CPU 100*a* determines whether or not the average luminance of the captured image G exceeds a predetermined value (step S108), and when the luminance does not exceed the predetermined value, there is an adjustment of the amount of current flowing to the light-emitting diodes L1 and L2 using the light source section input/output interface 100*d* to adjust the amount of light (step S109), whereupon the process returns to step S107.

When the average luminance of the captured image G exceeds the predetermined value (step S108: YES), the CPU 100*a* performs the same process as step S105 on the image obtained in step S107 to prepare a luminance profile PF2 and a concentration profile NP2 which is independent of the amount of entering light as shown in FIGS. 8 and 9.

The CPU 100*a* then respectively calculates the peak height h1 and center coordinate cg1 from the concentration profile NP1 obtained in step S105 and the peak height h2 and center coordinate cg2 from the concentration profile NP2 obtained in step S110, then calculates the blood vessel depth index S as an index which reflects the depth of the blood vessel via equation (1) below using these calculated values. The CPU 100a also stores the calculation results in the frame memory 100e (step S111).

$$S=(cg2-cg1)/\{(h1+h2)/2\} \qquad (1)$$

The CPU 100a also calculates the amount of light and light ratios of the light sources (light-emitting diodes R1 and R2 and the light-emitting diodes L1 and L2) on the right and left of the blood vessel (step S112) based on the luminance profile PF1 obtained in step S105 and the luminance profile PF2 obtained in step S110, and executes a process to adjust the amount of light of the light-emitting diodes R1 and R2 and the light-emitting diodes L1 and L2 so as to make the luminance profiles PF1 and PF2 symmetrical on right and left (step S113).

The CPU 100a then executes a process to control the light source section input/output interface 100d and illuminate the imaging region CR (refer to FIG. 13) by the light-adjusted light-emitting diodes R1, R2, L1, and L2, and then image this region via the imaging section 8 (step S114). The CPU 100a determines the average luminance of the image G captured in step S114, and determines whether or not the average luminance exceeds a predetermined value (step S115). When the average luminance does not exceed the predetermined value, an error message is displayed (step S116), and the process returns to step S101.

Figure 10:
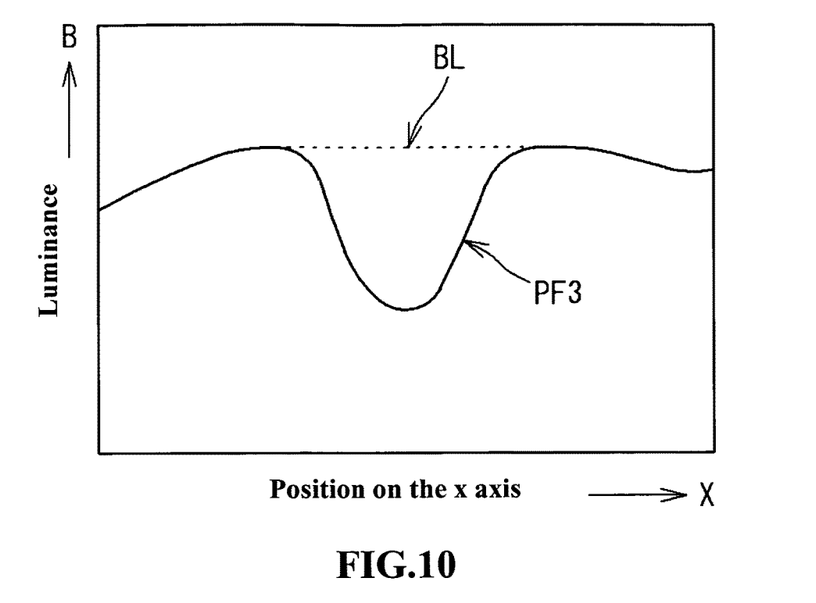
FIG. 10 shows the luminance distribution in a direction which transects the blood vessel at the y coordinate value (480) of the captured image G.

FIG. 10 shows the distribution of the luminance in a direction which transects the blood vessel at the y coordinate (480) of the captured image G.

Figure 11:
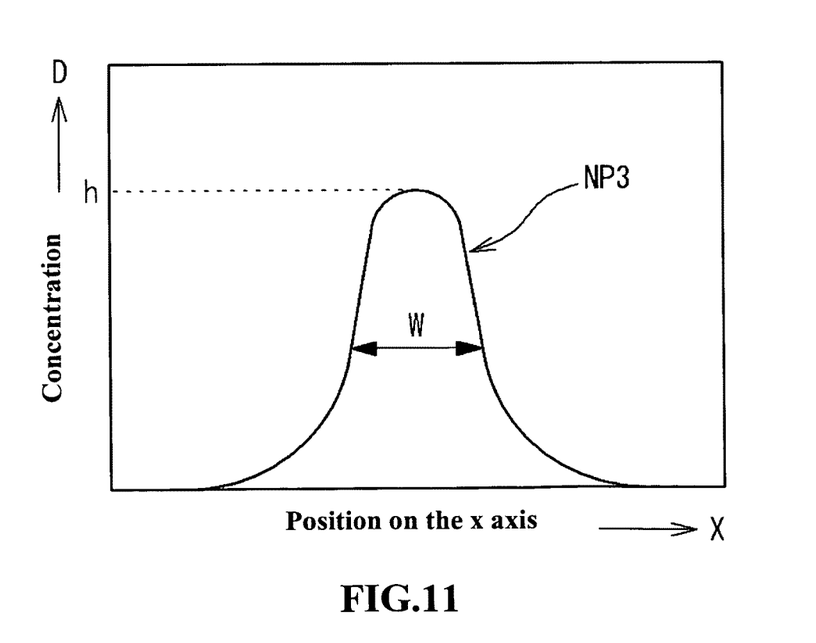
FIG. 11 shows the distribution of hemoglobin concentration in a direction which transects the blood vessel at the y coordinate value (480) of the captured image G.

FIG. 11 shows the distribution of hemoglobin concentration in a direction which transects the blood vessel at the y coordinate value (480) of the captured image G. When the average luminance of the captured image G exceeds the predetermined value (step S115: YES), the CPU 100a sets the y coordinate value of the calculation object of the obtained image G at (480) which becomes the center in the y axis direction of the image, then the luminance values are determined from end to end at the y coordinate value (480) of the captured image G, and a luminance profile PF3 is prepared which has a distribution in a direction which transects the blood vessel as shown in FIG. 10. The CPU 100a then reduces the noise component of the obtained luminance profile PF3 using a high-speed Fourier transform method, and thereafter standardizes the luminance profile PF3 at baseline BL to prepare a concentration profile NP3 as shown in FIG. 11 (step S117). Since the baseline BL basically determines the shape of the luminance profile of the part absorbed by the blood vessel, it is possible to obtain a concentration profile NP3 which is independent of the amount of entering light.

The CPU 100a then calculates the average width w as the distribution width corresponding to the peak height h and blood vessel diameter based on the prepared concentration profile NP3. The average width w is the distribution width at 50% of the peak height of the concentration profile NP3. The obtained peak height h represents the ratio of the intensity of the light which has passed through the tissue part and the intensity of the light absorbed by the blood vessel (blood) of the measurement object, and average width w represents the length equivalent to the blood vessel diameter in a direction perpendicular the imaging direction. The CPU 100a then calculates the uncorrected hemoglobin concentration D using equation (2) below, and stores the result in the frame memory 100e. (step S118).

$$D=h/w^n \qquad (2)$$

Where n is a constant which represents the nonlinearity of the spread of the average width due to scattering. When there is no light scattering, n=1, and n>1 when there is light scattering.

The CPU 100a then calculates the tissue blood index M which represents the amount of blood contained in the peripheral tissue based on the blood vessel peripheral tissue image of the captured image G obtained in step S114 (step S119).

Thus, although the uncorrected hemoglobin concentration D is determined based on the peak height h of the concentration profile NP3, the peak height h is relatively determined based on the ratio of the tissue blood concentration around the blood vessel. That is, the uncorrected hemoglobin concentration D may vary depending on whether there is much or little tissue blood around the blood vessel.

In the present embodiment, the tissue blood index M is calculated based on the image of the tissue surrounding the blood vessel in the captured image, and the uncorrected hemoglobin concentration is corrected based on the tissue blood index M. The corrected hemoglobin concentration can therefore be measured independent of individual differences in the amount of peripheral tissue blood or an increase in the amount of peripheral tissue blood caused by blood congestion when the cuff is tightened. This process will be described later.

The CPU 100a derives a correction count fs based on the blood vessel depth index S calculated in step S11, and a correction coefficient fm based on the tissue blood index M calculated in step S119, and calculates a corrected hemoglobin concentration Do by equation (3) below using the derived data (step S120).

$$Do=D\times fs\times fm \qquad (3)$$

Note that the correction coefficient fm based on the tissue blood index M is derived based on the function fm=f(M) so that the correction coefficient fm=1 when the value of the obtained M matches the statistically determined average value. Since, as the amount of blood increases in the tissue, so the ratio of light from the light source that is absorbed in the area outside the blood vessel also increases and the difference in the luminance between the peripheral tissue and the measurement object blood vessel decreases (the peak height h of the concentration profile NP3 becomes smaller in FIG. 11), the uncorrected hemoglobin concentration D calculation becomes too small. The correction coefficient fm must be a correctable coefficient so as to be proportional to the amount of tissue blood and increase the uncorrected hemoglobin concentration D; therefore, it is desirable that a linear function which has a positive slope is used as the function fm=f(M).

An accurate hemoglobin concentration considering the amount of blood in the tissue can therefore be calculated without using a complex calculation method by using a configuration in which the precorrected hemoglobin concentration calculated based on the blood vessel image is corrected based on the tissue blood index M.

The CPU 100a stores the calculation result of step S121 in the frame memory 100e (step S121), and returns to the main routine.

Figure 12:
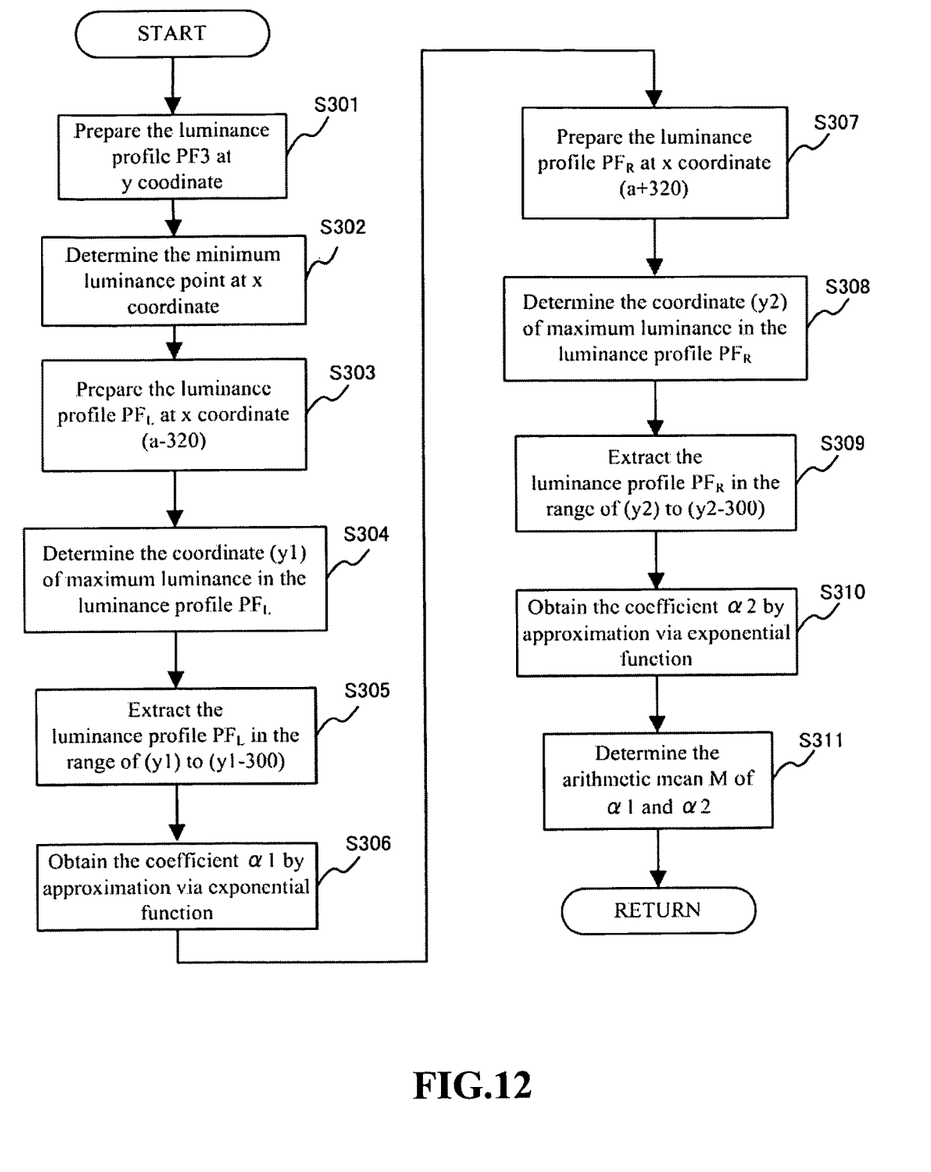
FIG. 12 is a flow chart showing details of the process for determining a tissue blood index M in step S119 of FIG. 6.

FIG. 12 is a flow chart showing details of the process for determining a tissue blood index M in step S119 of FIG. 6. The process for calculating the tissue blood index M in step S119 is described below using FIG. 12.

The CPU 100a sets the y coordinate value of the calculation object at (480) as the center in the y axis direction of the image G captured in step S114 of FIG. 6, determines the luminance of the pixels of the x coordinates from end to end at the set y coordinate value (480), and prepares a luminance profile PF4 which has a distribution in a direction which transects the blood vessel.

Figure 13:
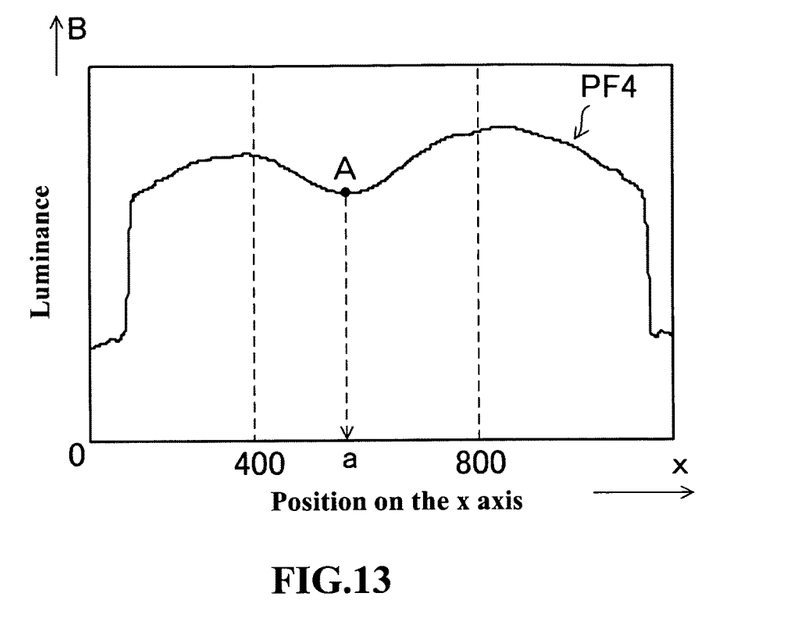
FIG. 13 shows the luminance distribution in a direction which transects the blood vessel at the y coordinate value (480) of the captured image G.

FIG. 13 shows the luminance distribution in a direction which transects the blood vessel at the y coordinate value (480) of the captured image G.

The CPU 100a then determines the X coordinate (a) at lowest luminance point (hereinafter referred to as "minimum luminance point") A within the 400×800 range of the horizontal direction luminance profile PF4 prepared in step S301 (step S302). In the determination of the minimum luminance point within the 400×800 range, the bilateral left and right end areas of the captured image G have low luminance due to the lack of penetration of the light from the light-emitting diodes L1, L2, R1 and R2 provided above and below the paper surface of the imaging region CR (refer to FIG. 5), and these areas are therefore extracted to determine the position of the blood vessel. The position of the x coordinate (a) determined above becomes the position of the blood vessel in the captured image.

The luminance in the captured image G reflects the amount of light absorbed by the blood when the light passes perpendicular to the blood vessel, and, thus, reflects the distance of the passage of the light within the blood. Since the cross section of the blood vessel is approximately circular, when the light passes perpendicularly through the blood vessel, the distance of the passage of the light within the blood is longest at the center position of the blood vessel, and most light is absorbed at the center position of the blood vessel. Looking at the luminance profile PF4 in which luminance distribution is in a direction which transects the blood vessel, the point of lowest luminance becomes the center position of the blood vessel.

Since the luminance of the captured image reflects the amount of blood, the accurate position of the blood vessel can therefore be determined by a configuration in which the position of the blood vessel is determined based on the luminance distribution in a direction which transects the blood vessel.

The CPU 100a then determines the luminance of the pixels of the y coordinates from end to end at x coordinate (a−320) based on the x coordinate (a) of the of lowest luminance point A (refer to FIG. 7) determined in step S302, and prepares a luminance profile $PF_L$ with a distribution along the blood vessel on the right side of the blood vessel (step S303).

The x coordinate used in preparing the luminance profile $PF_L$ is set at (a−320) because there are 320 pixels per quadrant when the image is divided into four equal quadrants according to the coordinate division of the image into 0×1280. Although the value of the x coordinate (a−320) used to prepare the luminance profile $PF_L$ may be suitably changed, the x coordinate is desirably set at a position at least somewhat separated from x coordinate (a) of the blood vessel position so as to avoid overlapping the blood vessel because the luminance profile must be prepared based on the peripheral tissue area that does not overlap the blood vessel.

In the present embodiment, the luminance profile is prepared by determining the position of the blood vessel in the captured image, and is based on a position a set distance from the blood vessel position. According to this configuration an accurate blood component concentration can be determined without fluctuations of the measurement results caused by the position at which the device is mounted because the peripheral tissue blood index M is normally determined based on a position at a fixed distance from the blood vessel even when, for example, the blood vessel in the captured image is laterally shifted to one side in the captured image due to the position at which the device is mounted.

Figure 14:
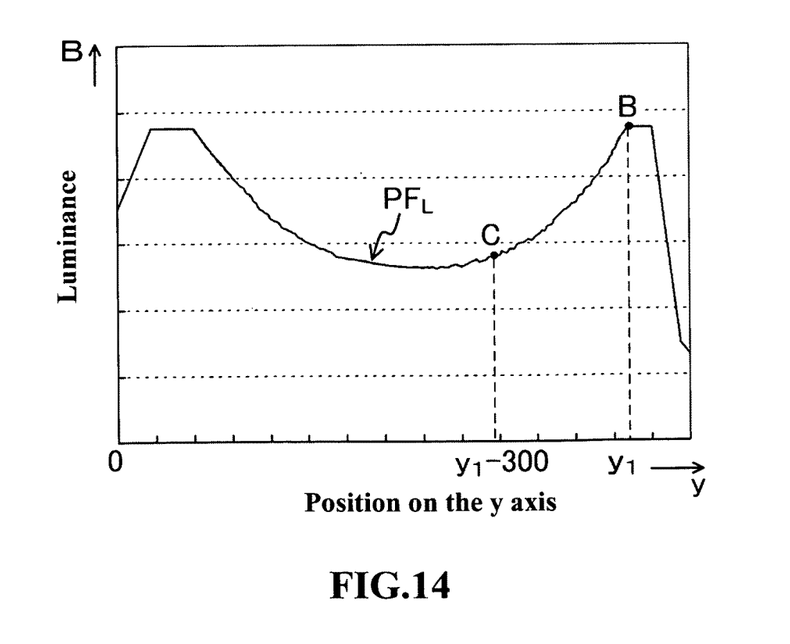
FIG. 14 shows the luminance distribution which is distributed along the x coordinate value (a–320) of the captured image G.

FIG. 14 shows the distribution of the luminance distributed along the blood vessel at the x coordinate value (a−320) of the captured image G; luminance is plotted on the vertical axis, and the position on the y coordinate in the captured image G is plotted on the horizontal axis. The CPU 100a determines the y coordinate value (y1) of position B (refer to FIG. 7) at which luminance reaches the saturation point and at which the y coordinate value is greater than the minimum luminance point in the luminance profile $PF_L$ prepared in step S304) (step S304).

Figure 15:
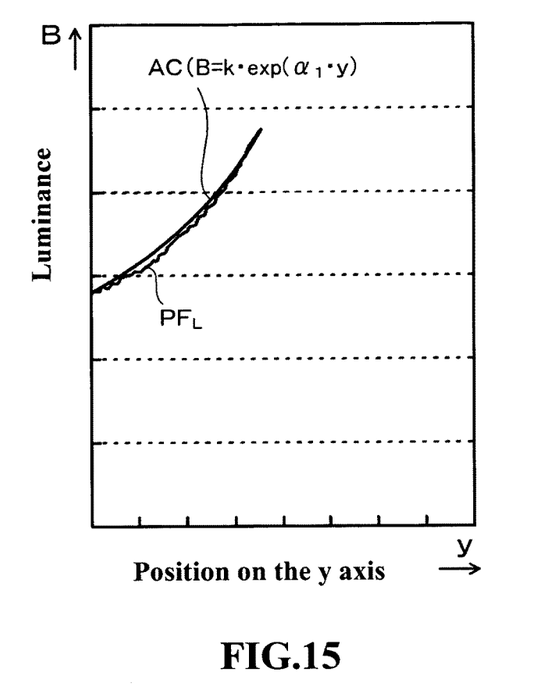
FIG. 15 is an illustration of a predetermined region extracted from the luminance distribution of FIG. 14.

The CPU 100a then extracts a range (y1-300) to (y1) (the range from point B to point C in FIG. 7) from the luminance profile $PF_L$ (step S305). FIG. 15 shows an example of an extracted luminance profile.

The reason that only the range (y1-300) to (y1) of the luminance profile $PF_L$ is extracted is described below. When the peripheral tissue around the blood vessel is relatively homogeneous, the light from the light source attenuates according to an exponential function, and the luminance profile $PF_L$ of FIG. 14 is thought to attain a parabolic shape in which the exponential functions of mutually opposite directions overlap due to the disposition of the light-emitting diode light sources above and below the imaging region CR. That is, the area near the center in the y coordinate direction of the captured image G is an area in which the light overlaps from the light sources disposed on both the top and bottom sides, and this area must be excluded from the analysis object because it is not an area which directly reflects the amount of light absorbed by the peripheral tissue. The point of luminance saturation in the luminance profile $PF_L$ is the point at which the light from the light-emitting diodes disposed on the bottom side of the imaging region CR reaches 100%, so this area must also be removed from the analysis object because it is not an area in which light from the light source is absorbed by the peripheral tissue. In the present embodiment, analysis is performed after extracting only the luminance profile within a predetermined range from the point of luminance saturation in order to only extract the area in which light is actually absorbed by the peripheral tissue and calculate the attenuation rate of the light.

The CPU 100a then approximates the extracted luminance profile $PF_L$ by the exponential function $B=k \cdot \exp(\alpha \cdot y)$ such as the function curve AC shown in FIG. 15, and stores the value of the obtained function αa in the frame memory 100e (step S306).

The CPU 100a then determines the luminance of the pixels from end to end at the x coordinate (a−320) and the x coordinate (a+320) symmetrical to the axis of the blood vessel based on the x coordinate (a) of the blood vessel position determined in step S302, and prepares a luminance profile $PF_R$ with a distribution along the blood vessel on the right side of the blood vessel (step S307). The CPU 100a executes the same process as steps S304 through S306 for the luminance profile $PF_R$ prepared in step S307 to obtain α2, which is then stored in the frame memory 100e (steps S308 through S310).

The CPU 100a then reads the coefficient α1 and coefficient α2 from the frame memory 100e, and determines the arithmetic mean M (step S311). The CPU 100a stores the obtained value of M in the frame memory 100e, and the process returns to the main routine. The obtained value of M becomes the tissue blood index.

The tissue blood index M is discussed below.

The exponential function $B=k \cdot \exp(\alpha \cdot y)$ used in step S306 is a function configured by the luminance B and the position information y on the image. The function represents the attenuation of the luminance B by the ratio of $\exp(-\alpha 1)$ when y is −1. That is, the coefficient α1 determined thusly is a coefficient which determines the attenuation rate of the light when the light from the light source moves within the living tissue of one pixel in the captured image G.

The coefficient α1 can be used as an index which reflects the concentration of the hemoglobin contained in the peripheral tissue. That is, the light from the light source is absorbed by the hemoglobin contained in the peripheral tissue according to Beer's law; when considering the light reaching the imaged part, the amount of light I which enters the imaged part is expressed by the equation below.

$$I = I_o \cdot \exp(-\epsilon \epsilon \cdot c \cdot L) \quad (4)$$

(In the expression, $I_o$ represents the amount of light from the light source, $\epsilon$ represents the absorption coefficient, c represents the concentration, and L represents the distance the light moves within the medium.)

In equation (4), the attenuation rate of the light per unit distance L is determined by the product of the absorption coefficient $\epsilon$ and the concentration c. Thus the following expression obtains.

$$\alpha 1 = \epsilon \cdot c \quad (5)$$

Since the hemoglobin absorption coefficient $\epsilon$ is constant, the coefficient α1 is understood to reflect the amount of blood in peripheral tissue, that is, the concentration c of the hemoglobin contained in the peripheral tissue. Since the tissue blood index M is calculated by the arithmetic mean of the coefficient α1 which reflects the amount of blood in the peripheral tissue present on the left side of the blood vessel and the coefficient α2 which reflects the amount of blood in the peripheral tissue present on the right side of the blood vessel, the tissue blood index M is understood to be an index which reflects the amount of blood in the peripheral tissue present on bilateral sides of the blood vessel.

Furthermore, the coefficient α2 is determined at a position on a symmetrical axis of the blood vessel based on the same process as used for the coefficient α1, and the following effect is obtained by using the arithmetic mean M of the coefficient α1 and the coefficient α2 as the tissue blood index. For example, although it is possible that a hemoglobin concentration which reflects an accurate tissue blood quantity may not be obtained when the tissue blood index M is calculated based on peripheral tissue present on the right and left sides of the blood vessel when a blood vessel which branches off from the measurement object blood vessel is present in the peripheral tissue, and when the blood in the peripheral tissue is nonuniform due to congestion caused by the tightening of a cuff or the like, accurate hemoglobin concentration can be measured with excellent reproducibility without large fluctuations of the tissue blood index M produced by these causes.

Figure 16:
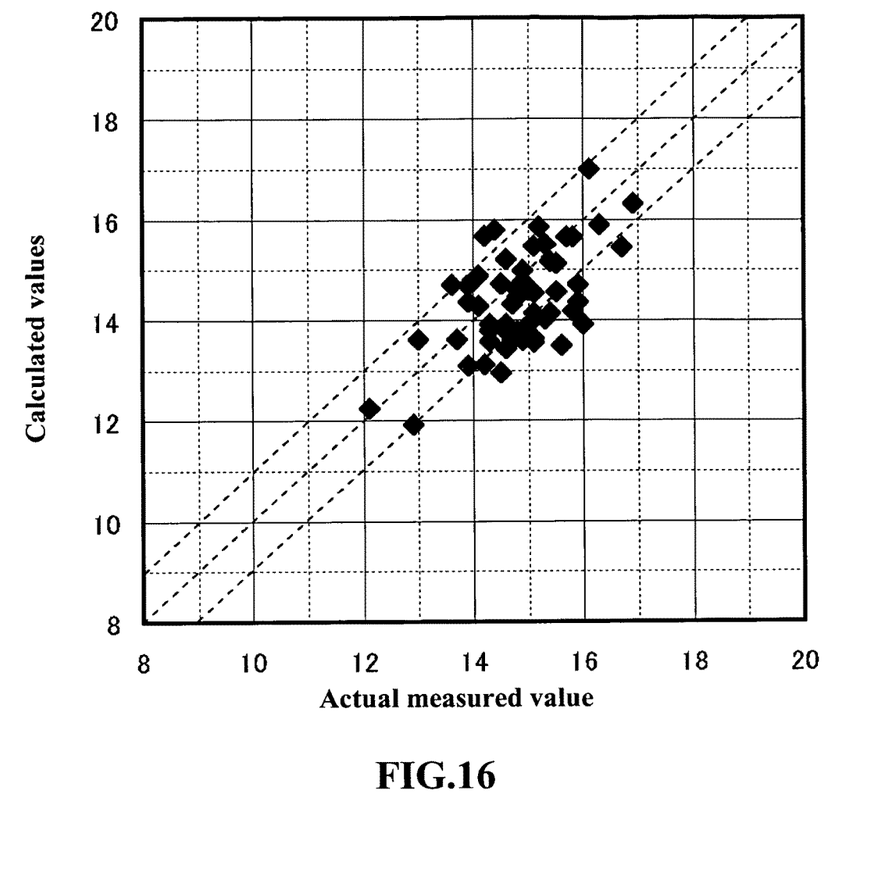
FIG. 16 is a graph which plots the actual values obtained from a hemocyte counter and the calculated values which were calculated by the non-invasive blood component measuring device of the present embodiment based on the hemoglobin concentration of a plurality of subjects.

FIG. 16 is a graph showing the hemoglobin concentrations of a plurality of subjects by plotting the values calculated by the device 1 of the embodiment of the present invention and the actual measured values obtained by a blood cell counter or the like. As shown in FIG. 16, the error between the actual measured values and the values calculated by the device 1 converge within the range of approximately 1 g/dL, so it is understood that the device 1 is capable of measuring hemoglobin concentration with high precision since there is no divergence between the actual measured values and the calculated values.

Note that although the light source sections is configured by four light-emitting diodes R1, R2, L1 and L2 in the present embodiment, the number of light-emitting diodes is not limited to this example inasmuch as the number may be suitably increased or decreased.

Although the present embodiment has been described by way of example of a blood component measuring device for measuring hemoglobin concentration, the scope of the present invention is not limited to this example and may be variously modified insofar as the device measures information of a living body based on an image obtained by imaging the living body. For example, the present invention is also applicable to devices which measure blood flow rate and blood flow amount by continuous imaging of the wrist part.

What is claimed is:

1. A non-invasive blood component measuring device comprising:
    a light source section for illuminating a living body which includes a blood vessel;
    an imaging section for capturing a living body image of the living body illuminated by the light source section;
    a controller, including a memory under control of a processor, the memory storing instructions enabling the processor to carry out operations, comprising:
        calculating, based on an image of a blood vessel shown in the living body image, a concentration of a blood component in blood of the living body;
        determining a position of the image of the blood vessel in the living body image;
        generating a first luminance distribution representing a distributed luminance of pixels lined along the image of the blood vessel, the pixels being apart from the image of the blood vessel by a predetermined distance;
        obtaining, based on the first luminance distribution, an index which represents an amount of blood contained in a peripheral tissue of the blood vessel; and
        correcting, based on the index, the concentration of the blood component.

2. The device of claim 1 wherein,
    the operations further comprise:
        generating a second luminance distribution representing a distribution of luminance of pixels lined across the image of the blood vessel; and
        determining, based on the second luminance distribution, the position of the image of the blood vessel.

3. The device of claim 2 wherein,
    the operations further comprise generating a third luminance distribution representing a distribution of luminance of pixels lined along one side of the image of the blood vessel, the pixels being apart from the image of the blood vessel by a predetermined distance, wherein the first luminance distribution is made based on pixels lined along the other side of the image of the blood vessel, and the index is obtained based on the first luminance distribution and the third luminance distribution.

4. The device of claim 3 wherein, the operations further comprise generating a fourth luminance distribution representing a distribution of luminance of pixels lined across the image of the blood vessel, and wherein,
    the calculation of the concentration is performed based on the fourth luminance distribution.

5. The device of claim 1 wherein, the blood component is hemoglobin.

6. A non-transitory computer program product comprising:
    a computer readable medium; and
    instructions, on the computer readable medium, adapted to enable a non-invasive blood component measuring device, comprising a light source section for illuminating a living body containing a blood vessel and an imaging section for capturing a living body image of the living body which is illuminated by the light source section, to perform operations, comprising:
- calculating, based on an image of a blood vessel shown in the living body image, a concentration of a blood component in blood of the living body;
- determining a position of the image of the blood vessel in the living body image;
- generating a first luminance distribution representing a distribution of luminance of pixels lined along the image of the blood vessel, the pixels being apart from the image of the blood vessel by a predetermined distance;
- obtaining, based on the first luminance distribution, an index which represents an amount of blood contained in a peripheral tissue of the blood vessel; and
- correcting, based on the index, the concentration of the blood component.

7. The computer program product of claim 6 wherein, the operations further comprise:
- generating a second luminance distribution representing a distribution of luminance of pixels lined across the image of the blood vessel; and
- determining, based on the second luminance distribution, the position of the image of the blood vessel.

8. The computer program product of claim 7 wherein, the operations further comprise generating a third luminance distribution representing a distribution of luminance of pixels lined along one side of the image of the blood vessel, the pixels being apart from the image of the blood vessel by a redetermined distance, wherein the first luminance distribution is made based on pixels lined along the other side of the image of the blood vessel, and wherein,
- the index is obtained based on the first luminance distribution and the third luminance distribution.

9. The computer program product of claim 8 wherein, the operations further comprise generating a fourth luminance distribution representing a distribution of luminance of pixels lined across the image of the blood vessel, and wherein,
- the calculation of the concentration is performed based on the fourth luminance distribution.

10. The computer program product of claim 6 wherein, the blood component is hemoglobin.

* * * * *